United States Patent [19]

Haley

[11] Patent Number: 5,270,466
[45] Date of Patent: Dec. 14, 1993

[54] SUBSTITUTED QUINAZOLINE FUNGICIDAL AGENTS

[75] Inventor: Gregory J. Haley, Langhorne, Pa.

[73] Assignee: American Cyanamid Company, Wayne, N.J.

[21] Appl. No.: 897,178

[22] Filed: Jun. 11, 1992

[51] Int. Cl.$^5$ .................. A01N 43/54; C07D 239/94; C07D 239/95; C07D 239/93
[52] U.S. Cl. .................................. 544/293; 544/62; 544/116; 544/119; 544/285; 544/286; 544/287; 544/291
[58] Field of Search ............... 544/62, 116, 119, 285, 544/286, 287, 291, 293

[56] References Cited

U.S. PATENT DOCUMENTS 5,180,419  1/1993  Gange .................................. 504/276
5,185,027  2/1993  Vogelbacher ...................... 504/219

FOREIGN PATENT DOCUMENTS 55-007243A  1/1980  Japan .

OTHER PUBLICATIONS

Wessely et al., Monat Chem 93, 77 (1962).
A. Albert and A. Hampton, Journal of The Chemical Society, pp. 4985–4993 (1952).
R. Iyer, N. Anand and M. Dhar, Journal of Science and Industrial Research, 13b, pp. 451–452 (1954).
B. Kaushiva, Annals of Biochemistry and Experimental Medicine, 20, supplement, pp. 493–504 (1960).
R. Iyer, N. Anand and M. Dhar, Journal of Science and Industrial Research, 15c, pp. 1–7 (1956).
A. Albert and A. Hampton, Journal of The Chemical Society, pp. 505–513 (1954).
G. Malesani, F. Marcolin and G. Rodighiero, Advances in Antimicrobial and Antineoplastic Chemotherapy, Progress in Research and Clinical Application, Proceedings of the International Congress of Chemotherapy, 7th, Prague, Aug. 23-28, 1971, vol. 1, ed. M. Hejzlar (Baltimore: University Park Press, 1972), pp. 1081–1083.
G. Malesani, et al., Farmaco, Edizione Scientifica, 27, pp. 731–743 (1972).
G. Malesani, et al., Chimica Therapeutica, 5, pp. 255–260 (1970).
A. Albert, et al., British Journal of Experimental Pathology, 35, pp. 75–84 (1954).

Primary Examiner—Mark L. Berch
Attorney, Agent, or Firm—Michael P. Morris

[57] ABSTRACT

There are provided substituted quinazoline compounds of formula I

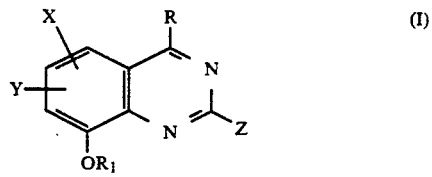

and their use for the prevention, control or amelioration of diseases caused by phytopathogenic fungi. Further provided are compositions and methods comprising those compounds for the protection of plants from fungal infestations and diseases.

4 Claims, No Drawings

SUBSTITUTED QUINAZOLINE FUNGICIDAL AGENTS

BACKGROUND OF THE INVENTION

Phytopathogenic fungi are the causal agents for many diseases that infect and destroy crops. In particular, the diseases sugar beet cercospora leaf spot, tomato early blight, apple scab and grape botrytis are especially devastating.

Sugar beet is susceptible to many foliar diseases caused by fungi. One of the most frequently encountered and destructive foliar diseases occurring on sugar beet is sugar beet cercospora leaf spot, caused by the fungus, *Cercospora beticola*. Sugar beet cercospora leaf spot is common to sugar beet throughout the world, and is particularly destructive in regions with wet, warm growing seasons, such as Western and Southern Europe and the Midwestern United States. During periods of high temperature and wetness, sugar beet cercospora leaf spot spreads rapidly. Ultimately, the disease kills sugar beet leaf tissue, resulting in reduced beet weight and sugar content.

Tomatoes are also susceptible to diseases caused by fungi. For example, the foliage, stem and fruit of the tomato plant may be attacked by a fungus, *Alternaria solani*, resulting in a disease called tomato early blight. Tomato early blight occurs wherever tomatoes are grown, but is most destructive in regions with wet, humid climates. Uncontrolled, tomato early blight causes the defoliation of the tomato plant, resulting in reduced fruit number and size.

The leaves and fruit of apple trees are susceptible to attack by a fungus, *Venturia inaequalis*, resulting in a disease called apple scab. The disease occurs wherever apples are grown, but is most common in the United States and Europe. Uncontrolled, apple scab results in deformed, low quality fruit.

Grapes and peppers are susceptible to attack caused by the fungus, *Botrytis cinerea*, causing grape botryitis and pepper botryitis. Grape botrytis, for example, is an especially destructive disease that destroys the cell walls of the fruit, resulting in bunch rot. Grape botrytis occurs wherever grapes are grown, but is most common in Europe.

In spite of the commercial fungicides available today, diseases caused by fungi still abound. Accordingly, there is ongoing research to create new and more effective fungicides for controlling or preventing fungal infestations.

Certain quinazolines are known to possess useful biological activity (see, e.g., The Journal of Science and Industrial Research, 15c, pages 1-7 (1956) and 13b, pages 451-452 (1954); Advances in Antimicrobial and Antineoplastic Chemotherapy, Progress in Research and Clinical Application, Proceedings of the International Congress of Chemotherapyl 7th, Prague, Aug. 23-28, 1971, Volume 1, ed. M. Hejzlar (Baltimore: University Park Press, 1972), pages 1081-1083; and Annals of Biochemistry and Experimental Mediciner 20, supplement, pages 493-504 (1960)). However, none of these documents refer to any fungicidal activity for such compounds.

It is therefore an object of the present invention to provide substituted quinazoline compounds which are highly effective for controlling or preventing phytopathogenic fungal infestations in agronomic crops, both growing and harvested.

It is also an object of the present invention to provide a method for the prevention, control or amelioration of a disease caused by a phytopathogenic fungus by contacting said fungus with a fungicidally effective amount of a substituted quinazoline compound.

These and other objects of the present invention will become more apparent from the detailed description thereof set forth below.

SUMMARY OF THE INVENTION

The present invention describes substituted quinazoline compounds which are useful as fungicidal agents for the protection of plants from fungal infestations and diseases.

The substituted quinazoline compounds of the present invention have the following structural formula I:

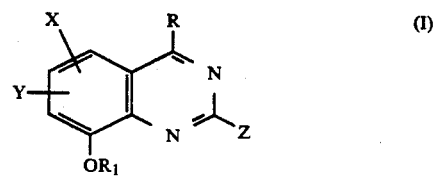

wherein
X, Y and Z are each independently hydrogen, halogen,
  $C_1$–$C_6$ alkyl optionally substituted with one or more halogen atoms,
  $C_1$–$C_6$ alkoxy optionally substituted with one or more halogen atoms,
  nitro, or
  cyano;
R is $NR_2R_3$ or $AR_4$;
A is O or S;
$R_2$ and $R_3$ are each independently hydrogen,
  $C_1$–$C_6$ alkyl optionally substituted with one or more halogen atoms, nitro groups, cyano groups, or $C_1$–$C_4$ alkoxy groups optionally substituted with one or more halogen atoms, or
  phenyl optionally substituted with one to three halogen atoms, nitro groups, cyano groups, $C_1$–$C_4$ alkyl groups optionally substituted with one or more halogen atoms, or $C_1$–$C_4$ alkoxy groups optionally substituted with one or more halogen atoms; and,
  when taken together, $R_2$ and $R_3$ may form a 5- or 6-membered ring in which $R_2R_3$ is represented by the structure: —$(CH_2)_n$—, optionally interrupted by O, S or N, where n is an integer of 3, 4 or 5;
$R_4$ is $C_1$–$C_6$ alkyl optionally substituted with one to three halogen atoms, nitro groups, cyano groups, or $C_1$–$C_4$ alkoxy groups optionally substituted with one or more halogen atoms, or
  phenyl optionally substituted with one to three halogen atoms, nitro groups, cyano groups, $C_1$–$C_4$ alkyl groups optionally substituted with one or more halogen atoms, or $C_1$–$C_4$ alkoxy groups optionally substituted with one or more halogen atoms;
$R_1$ is hydrogen,

or a metal, ammonium or organic ammonium cation;

$R_5$ is $C_1$-$C_6$ alkyl optionally substituted with one to three halogen atoms, or $C_1$-$C_4$ alkoxy groups optionally substituted with one or more halogen atoms, $C_2$-$C_6$ alkenyl optionally substituted with one to three halogen atoms, $C_3$-$C_6$ cycloalkyl optionally substituted with one to three halogen atoms, $C_1$-$C_4$ alkyl groups optionally substituted with one or more halogen atoms, or $C_1$-$C_4$ alkoxy groups optionally substituted with one or more halogen atoms, phenyl optionally substituted with one to three halogen atoms, nitro groups, cyano groups, $C_1$-$C_4$ alkyl groups optionally substituted with one or more halogen atoms, or $C_1$-$C_4$ alkoxy groups optionally substituted with one or more halogen atoms, $NHR_6$; or $OR_6$;

$R_6$ is $C_1$-$C_6$ alkyl optionally substituted with one to three halogen atoms, or $C_1$-$C_4$ alkoxy groups optionally substituted with one or more halogen atoms, or phenyl optionally substituted with one to three halogen atoms, nitro groups, cyano groups, $C_1$-$C_4$ alkyl groups optionally substituted with one or more halogen atoms, or $C_1$-$C_4$ alkoxy groups optionally substituted with one or more halogen atoms;

the acid addition salts thereof when $R_1$ is other than a cation;

the metal salts thereof; and the metal chelates thereof.

This invention also relates to compositions containing those compounds, and methods for using those compounds and compositions. Surprisingly, it has been found that the substituted quinazoline compounds of the present invention, and compositions containing them, are effective fungicidal agents for the prevention, control or amelioration of diseases caused by phytopathogenic fungi.

DETAILED DESCRIPTION OF THE INVENTION

Phytopathogenic fungi are the causal agents for many diseases which infect and destroy agronomic crops, both growing and harvested. In the United States alone, agronomic crops must compete with about 18,000 species of fungi. Accordingly, there is ongoing research to create new and more effective fungicides for preventing or controlling the vast array of fungal infestations of crops.

Advantageously, the present invention provides a method for the prevention, control or amelioration of a disease caused by a phytopathogenic fungus by contacting said fungus with a fungicidally effective amount of a formula 1, substituted quinazoline compound.

The present invention also provides a method for the protection of a plant, plant seed or tuber from fungal infestation and disease by applying to the plant, plant seed or tuber, or to the soil or water in which they are growing, a fungicidally effective amount of a formula I, substituted quinazoline compound.

The substituted quinazoline compounds of the present invention have the following structural formula I:

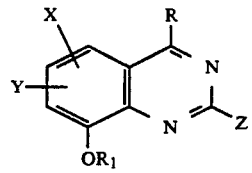

wherein

X, Y and Z are each independently hydrogen, halogen, $C_1$-$C_6$ alkyl optionally substituted with one or more halogen atoms, $C_1$-$C_6$ alkoxy optionally substituted with one or more halogen atoms, nitro, or cyano;

R is $NR_2R_3$ or $AR_4$;

A is O or S;

$R_2$ and $R_3$ are each independently hydrogen, $C_1$-$C_6$ alkyl optionally substituted with one or more halogen atoms, nitro groups, cyano groups, or $C_1$-$C_4$ alkoxy groups optionally substituted with one or more halogen atoms, or phenyl optionally substituted with one to three halogen atoms, nitro groups, cyano groups, $C_1$-$C_4$ alkyl groups optionally substituted with one or more halogen atoms, or $C_1$-$C_4$ alkoxy groups optionally substituted with one or more halogen atoms; and, when taken together, $R_2$ and $R_3$ may form a 5- or 6-membered ring in which $R_2R_3$ is represented by the structure: $-(CH_2)_n-$, optionally interrupted by O, S or N, where n is an integer of 3, 4 or 5;

$R_4$ is $C_1$-$C_6$ alkyl optionally substituted with one to three halogen atoms, nitro groups, cyano groups, or $C_1$-$C_4$ alkoxy groups optionally substituted with one or more halogen atoms, or phenyl optionally substituted with one to three halogen atoms, nitro groups, cyano groups, $C_1$-$C_4$ alkyl groups optionally substituted with one or more halogen atoms, or $C_1$-$C_4$ alkoxy groups optionally substituted with one or more halogen atoms;

$R_1$ is hydrogen,

or a metal, ammonium or organic ammonium cation;

$R_5$ is $C_1$-$C_6$ alkyl optionally substituted with one to three halogen atoms, or $C_1$-$C_4$ alkoxy groups optionally substituted with one or more halogen atoms, $C_2$-$C_6$ alkenyl optionally substituted with one to three halogen atoms, $C_3$-$C_6$ cycloalkyl optionally substituted with one to three halogen atoms, $C_1$-$C_4$ alkyl groups optionally substituted with one or more halogen atoms, or $C_1$-$C_4$ alkoxy groups optionally substituted with one or more halogen atoms, phenyl optionally substituted with one to three halogen atoms, nitro groups, cyano groups, $C_1$-$C_4$ alkyl groups optionally substituted with one or more halogen atoms, or $C_1$-$C_4$ alkoxy groups optionally substituted with one or more halogen atoms, $NHR_6$, or $OR_6$;

R₆ is C₁-C₆ alkyl optionally substituted with one to three halogen atoms, or C₁-C₄ alkoxy groups optionally substituted with one or more halogen atoms, or phenyl optionally substituted with one to three halogen atoms, nitro groups, cyano groups, C₁-C₄ alkyl groups optionally substituted with one or more halogen atoms, or C₁-C₄ alkoxy groups optionally substituted with one or more halogen atoms;

the acid addition salts thereof when R₁ is other than a cation;

the metal salts thereof; and the metal chelates thereof.

Preferred substituted quinazoline fungicidal agents of the present invention are those having structural formula II:

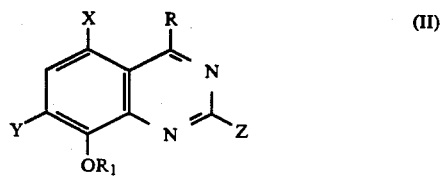

wherein X, Y, Z, R and R₁ are as described above.

Compounds of formula II which are particularly effective fungicidal agents are those wherein X is hydrogen, halogen or C₁-C₆ alkyl;

Y is hydrogen or halogen;

Z is hydrogen or C₁-C₆ alkyl optionally substituted with one or more halogen atoms;

R is NR₂R₃ or AR₄;

A is O;

R₂ and R₃ are each independently C₁-C₆ alkyl; and, when taken together, R₂ and R₃ may form a 5- or 6-membered ring in which R₂R₃ is represented by the structure: —(CH₂)ₙ—, optionally interrupted by O, where n is an integer of 3, 4 or 5;

R₄ is C₁-C₆ alkyl;

R₁ is hydrogen,

or an alkali metal, ammonium or organic ammonium cation;

R₅ is C₁-C₆ alkyl, C₃-C₆ cycloalkyl, phenyl, NHR₆, OR₆ or C₂-C₆ alkenyl optionally substituted with one halogen atom; and R₆ is C₁-C₆ alkyl or phenyl.

The present invention also relates to novel substituted quinazoline compounds having the structural formula

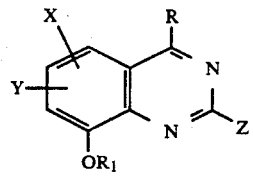

wherein X, Y, Z, R and R₁ are as described hereinabove for formula I with the proviso that when R₂ or R₃ is hydrogen, then X, Y, Z and R₁ cannot be hydrogen; and when X, Y, Z and R₁ are hydrogen, then R₂R₃ cannot represent the structure —(CH₂)₅—.

Exemplary of halogen hereinabove are fluorine, chlorine, bromine and iodine. Acid addition salt species of the present invention are those known in the art such as hydrogen halides, hydrogen sulfates, sulfonates, and the like. Metal cations include alkali metals, alkaline earth metals, manganese, copper, iron, zinc, cobalt, silver, nickel, and the like. Alkali metals include, for example, sodium, potassium and lithium, but sodium is generally preferred. This invention also includes organic ammonium salts. The term "organic ammonium" is defined herein as a group consisting of a positively charged nitrogen atom joined to from one to four aliphatic groups, each containing from one to sixteen carbon atoms. Metal salts are those known in the art such as ferric chloride hexahydrate, and the like. And metal chelates, when part of the present invention, are formed from metal complexes known in the art such as copper-(II) acetate, and the like.

Surprisingly, it has been found that the formula I compounds of the present invention are especially useful in the prevention, control or amelioration of diseases such as sugar beet cercospora leaf spot, apple scab, tomato early blight and grape or pepper botrytis which are caused by the phytopathogenic fungi *Cercospora beticola, Venturia inaequalis, Alternaria solani* and *Botrytis cinerea*, respectively.

We describe below generally useful methods for the preparation of the compounds of the invention. Formula I compounds wherein R is NR₂R₃ may be prepared as shown in Flow Diagram I.

FLOW DIAGRAM I

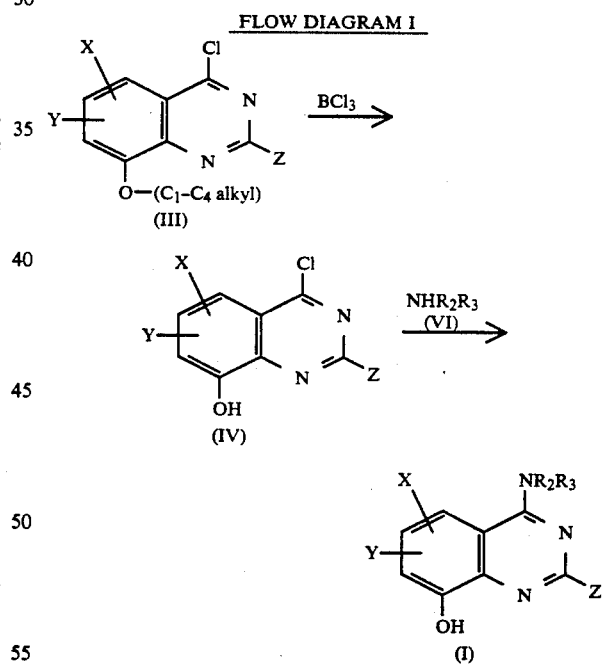

The appropriately substituted formula III 4-chloro-8-(C₁-C₄ alkoxy)quinazoline is reacted with at least one equivalent of boron trichloride in the presence of a chlorinated hydrocarbon solvent preferably at a temperature between about 20° C. and 80° C. to form the formula IV 4-chloro-8-hydroxyquinazoline. (Certain starting formula III compounds may be prepared according to the procedures described in The Journal of Science and Industrial Research, 15c, pages 1-7 (1956)). Said formula IV compound is then reacted with at least one equivalent of a formula VI amine in the presence of a chlorinated hydrocarbon solvent preferably at a temperature between about 0° C. and 40° C. to obtain the desired formula I compound. Compounds of formula I wherein R is $AR_6$ may be prepared as shown below in Flow Diagram II.

FLOW DIAGRAM II

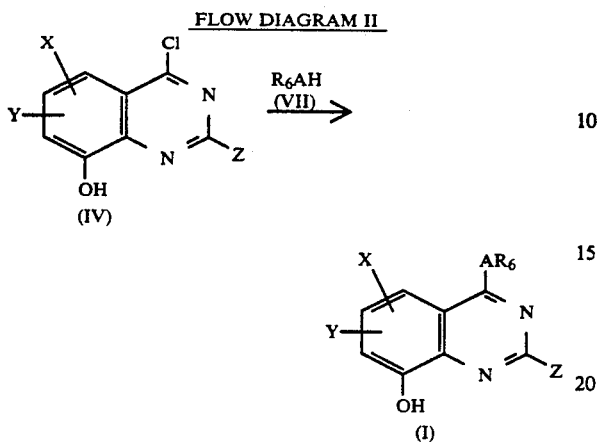

The above-prepared formula IV compound is reacted with at least one equivalent of a formula VII alcohol or thiol compound in the presence of a corresponding formula VII solvent or an inert organic solvent at a temperature between about 0° C. and 85° C. to obtain the desired formula I compound.

Other compounds of formula I wherein $R_1$ is —C(O)$R_5$ may be prepared by reacting the appropriately substituted formula I compound, wherein X, Y, Z and R are as described hereinabove for formula I and $R_1$ is hydrogen, with an appropriate formula VIII acid halide, in the presence of a base such as sodium hydride, to obtain the desired formula I compound having the same substituents as the starting material, but the hydroxyl group is replaced at the 8-position of quinazoline by —OC(O)$R_5$. The above reaction scheme is shown in Flow Diagram III.

FLOW DIAGRAM III

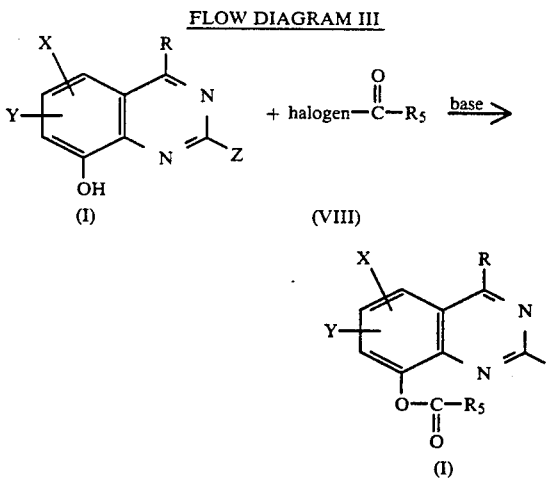

Further compounds of formula I wherein $R_5$ is $NHR_6$ may be prepared by reacting the appropriately substituted formula I compound wherein X, Y, Z and R are as described hereinabove for formula I and $R_1$ is hydrogen, with an appropriate formula IX isocyanante in the presence of an insert solvent. The resulting formula I compound has the same substituents as the starting material, but the hydroxyl group is replaced at the 8-position of quinazoline by —OC(O)$NHR_6$. The above reaction scheme is shown in Flow Diagram IV.

FLOW DIAGRAM IV

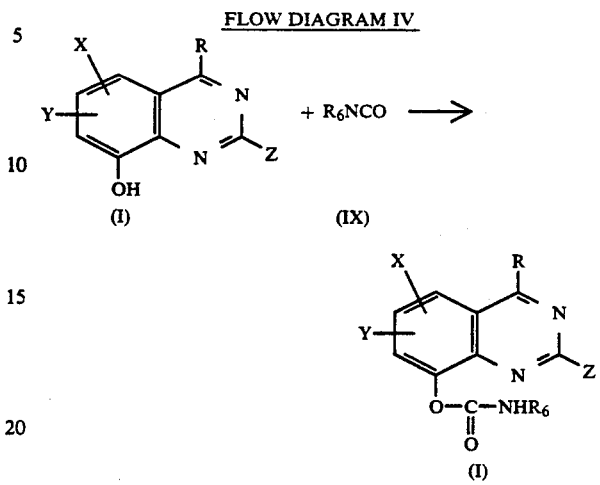

The substituted quinazoline compounds of the present invention are effective for preventing, controlling or ameliorating diseases caused by phytopathogenic fungi. The formula I compounds of the invention are especially useful for controlling or preventing the growth of phytopathogenic fungi such as *Cercospora beticola*, *Venturia inaequalis*, *Alternaria solani* and *Botrytis cinerea*. The formula I compounds of the invention are especially useful in the prevention, control or amelioration of diseases caused by phytopathogenic fungi such as sugar beet cercospora, apple scab, tomato early blight and grape or pepper botrytis.

The substituted quinazoline compounds of the present invention are also effective for controlling or preventing the growth of phytopathogenic fungi in the presence of growing or harvested plants when applied to said plants at fungicidally effective rates. The amount of compound necessary to be an effective fungicide will vary somewhat with the virulence of the target fungus, the environment of the treatment and other ambient conditions. In practice, generally about 20 ppm to 1,000 ppm, preferably about 50 ppm to 500 ppm, of the formula I compound dispersed in a liquid carrier when applied to the plant, seed or tuber, or to the soil or water in which they are growing, is effective to protect the plant, seed or tuber from fungal infestation and disease caused thereby.

The formula I compounds of the invention may be formulated into compositions as emulsifiable concentrates, flowable concentrates, or wettable powders which are diluted with water or other suitable polar solvent, generally in situ, and then applied as a dilute spray. Said compounds may also be formulated into compositions in dry compacted granules, granular formulations, dusts, dust concentrates, suspension concentrates, microemulsions, and the like. Such formulations lend themselves to seed, tuber, soil, water and/or foliage applications to provide the requisite plant protection. Such formulations include the compounds of the invention admixed with inert, solid or liquid diluents.

For example, wettable powders, dusts and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, about 1% to 5% by weight of a dispersing agent, such as sodium lignosulfonate, and about 1% to 5% by weight of a nonionic surfactant, such as octylphenoxy polyethoxy ethanol, nonylphenoxy polyethoxy ethanol, or the like.

A typical flowable liquid can be prepared by admixing about 40% by weight of the active ingredient with about 2% by weight of a gelling agent such as bentonite, about 3% by weight of a dispersing agent, such as sodium lignosulfonate, about 1% by weight of a thickener, such as polyethylene glycol, and water.

A typical emulsifiable concentrate can be prepared by dissolving about 15% to 70% by weight of the active ingredient in about 85% to 30% by weight of a solvent such as isophorone, toluene, butyl cellosolve, methyl acetate, propylene glycol monomethyl ether, or the like, and dispersing therein about 1% to 5% by weight of a nonionic surfactant, such as an alkylphenoxy polyethoxy alcohol.

The composition of the invention may be prepared for use by adding a predetermined quantity of formulated product, such as described above, to the desired volume of water or other suitable solvent, alone, or in combination with one or more other agronomic chemicals for simultaneous or sequential use.

Advantageously, the compounds of the invention may be used effectively in conjunction with, or in combination with, a fungicidally effective amount of one or more other biological chemicals, including but not limited to, anilazine, benalaxyl, benomyl, bitertanol, bordeaux mixture, carbendazim, carboxin, captafol, captan, chlorothalonil, cyproconazole, dichloran, diethofencarb, diniconazole, dithianon, dodine, edifenphos, fenarimol, fenbuconazole, fenfuram, fenpropidin, fenpropimorph, fentin hydroxide, ferbam, flusilazole, flusulfamide, flutriafol, folpet, fosetyl, fuberidazole, guazatine, hexaconazole, imazalil, iprobenfos, iprodione, mancozeb, maneb, metalaxyl, metiram, myclobutanil, nuarimol, ofurace, oxadixyl, oxycarboxin, penconazole, probenazole, prochloraz, propiconazole, pyrazophos, tebuconazole, thiabendazole, thiophanate, thiophanate-methyl, triadimefon, triadimenol, triarimol, tricyclazole, tridemorph, triflumizole, triforine, vinclozolin, zineb, and the like.

Where compositions of the invention are to be employed in combination treatments with other pesticidal agents, the composition may be applied as an admixture of the components as described above, or may be applied sequentially.

In order to facilitate a further understanding of the invention, the following examples are presented primarily for the purpose of illustrating more specific details thereof. The examples generally utilize the above reaction schemes and also provide further means for preparing even more compounds of the present invention which are not specifically described above. The invention should not be deemed limited by the examples as the full scope of the invention is defined in the claims.

EXAMPLE 1

Preparation of 4-Chloro-8-quinasolinol

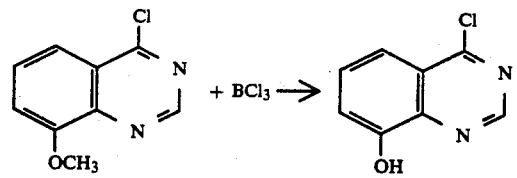

A solution of boron trichloride in dichloromethane (1.0 molar, 46.0 mi) is added via syringe to a solution of 4-chloro-8-methoxyquinazoline (2.24 g, 11.5 mmol) in chloroform, under a nitrogen atmosphere. The reaction mixture is heated at reflux for ½ hour, cooled to room temperature and diluted with a mixture of ice and saturated sodium bicarbonate solution. The phases are separated and the aqueous phase is extracted with chloroform. The organic phases are combined, washed with a 10% ethylenediaminetetraacetic acid (EDTA) solution, dried over $MGSO_4$ and concentrated in vacuo to obtain the title product as a white solid, 1.93 g (93%), mp >252° C.

Using essentially the same procedure and employing the appropriately substituted 4-chloro-8-methoxyquinazoline, the following compounds are obtained:

| X | Y | Z | mp °C. |
|---|---|---|---|
| H | H | $CH_3$ | green solid |
| H | H | $CF_3$ | white solid |
| Cl | H | H | >300 |
| $CH_3$ | H | H | 139–143 |
| Br | Br | H | brown solid |

EXAMPLE 2

Preparation of 7-Bromo-4,5-dichloro-8-quinazolinol

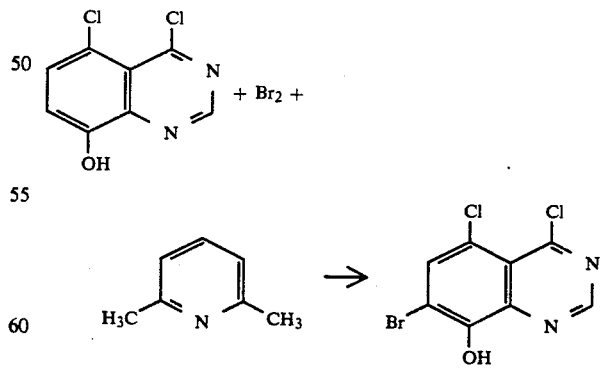

2,6-Lutidine (0.27 mL, 0.248 g, 2.32 mmol) is added to a solution of 4,5-dichloro-8-quinazolinol (0.5 g, 2.33 mmol) in chloroform at ice bath temperature. A solution of bromine in carbontetrachloride (2.4 mL, 1.0 molar) is then added dropwise to the reaction mixture and a precipitate forms. The reaction mixture is diluted with chloroform, washed sequentially with water and saturated NAHCO₃ solution, dried over MgSO₄ and concentrated in vacuo to give the title product as a yellow solid, 0.7 g, mp 156.5° C. (dec.).

Using essentially the same procedure and substituting 4-chloro-8-quinazolinol as starting material and using at least 2 equivalents of bromine, 5,7-dibromo-4-chloro-S-quinazolinol is obtained as a pale brown solid, mp 197.5°-199° C.

EXAMPLE 3

Preparation of 4-(Dinethylazino)-8-quinazolinol

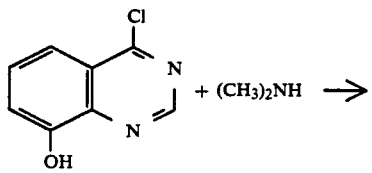 + (CH₃)₂NH →

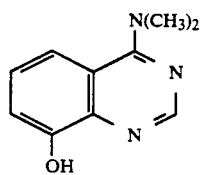

Dimethylamine gas is bubbled slowly through a solution of 4-chloro-8-quinazolinol (0.7 g, 3.88 mmol) in dichloromethane, under a nitrogen atmosphere, at 3° C. for 20 minutes. The cooling bath is removed and dimethylamine gas is bubbled through the reaction mixture for an additional 30 minutes. The reaction mixture is then concentrated in vacuo to obtain a grey solid. The solid is washed with water and extracted with 10% sodium hydroxide solution. The combined extracts are acidified to pH 7.0 and extracted with dichloromethane. The organic extracts are combined, dried over MGSO-4 and concentrated in vacuo to give the title product as a grey solid, 0.36 g, mp 104°-105° C.

Using essentially the same procedure and employing the appropriately substituted 4-chloro-8-quinazolinol and the appropriate amine, the following compounds are obtained:

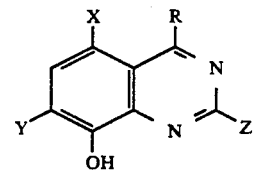

| X | Y | Z | R | mp °C. |
|---|---|---|---|---|
| H | H | H | morpholino | 121-122 |
| H | H | H | pyrrolidinyl | 174-175 |
| H | H | H | piperidinyl | 142.5-144 |
| Br | Br | H | N(CH₃)₂ | 146-147 |
| Br | Br | H | morpholino | green solid |
| Br | Br | H | pyrrolidinyl | green solid |
| H | H | CH₃ | N(CH₃)₂ | 77-78.5 |
| H | H | CF₃ | N(CH₃)₂ | 118-118.6 |
| CH₃ | H | H | N(CH₃)₂ | 137-138 |
| Cl | H | H | N(CH₃)₂ | 149.5-150.5 |
| Cl | Br | H | N(CH₃)₂ | 154-154.4 |

EXAMPLE 4

Preparation of 5-Chloro-4-isopropoxy-8-quinazolinol

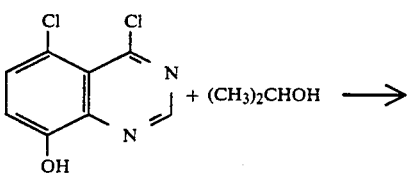 + (CH₃)₂CHOH →

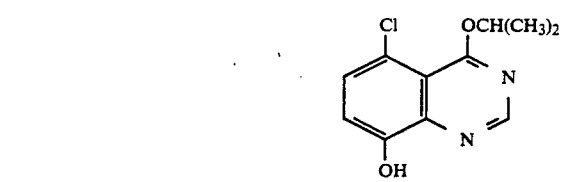

A mixture of 4,5-dichloro-8-quinazolinol (3.0 g, 13.95 mmol) in isopropanol is heated at reflux for 30 minutes, cooled to room temperature and filtered to obtain a solid. The solid is mixed with water and saturated NaHCO₃ solution. The resultant mixture is filtered and the filter cake is washed with water and dried to give the title product as an off-white solid, 1.71 g, mp 126°-126.5° C.

Using essentially the same procedure and employing the appropriately substituted 4-chloro-8-quinazolinol and the appropriate alcohol, the following compounds are obtained:

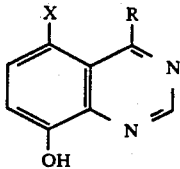

| X | R | mp °C. |
|---|---|---|
| Cl | O(CH₂)₂CH₃ | 139.5–139.8 |
| Cl | OCH₂CH₃ | 165.1–165.5 |
| Cl | OCH₃ | 184.3–184.7 |
| CH₃ | OCH₃ | 196–199 |

EXAMPLE 5

Preparation of
5-Chloro-4-(dimethylamino)-8-quinazolinyl acrylate

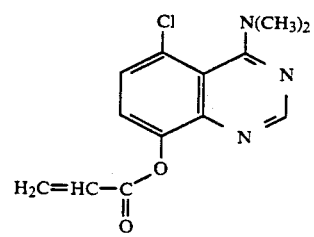

A solution of 5-chloro-4-(dimethylamino)-8-quinazolinol (0.65 g, 2.91 mmol) in N,N-dimethylformamide is treated in a single portion with a 60% sodium hydride dispersion in mineral oil (0.13 g, 3.25 mmol) at 50° C., stirred for 10 minutes, cooled to 10° C., treated with a solution of acryloyl chloride (0.29 g, 3.20 mmol) in tetrahydrofuran, stirred for 1 hour and diluted with ethyl acetate. The organic solution is washed sequentially with water and brine, dried over Na₂SO₄ and concentrated in vacuo to obtain a residue. Chromatography of the residue using silica gel and an ethyl acetate/heptane mixture gives the title product as a white solid, 0.42 g, mp 95°–100° C.

Using essentially the same procedure and employing the appropriately substituted 8-quinazolinol and the appropriate electrophile, the following compounds are obtained:

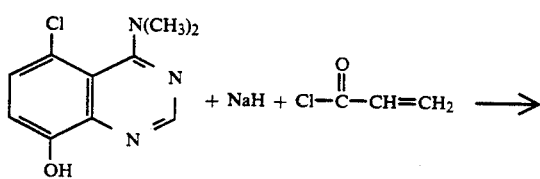

| X | Y | Z | R | R₁ | mp °C. |
|---|---|---|---|---|---|
| H | H | H | N(CH₃)₂ | —C(O)CH=CH₂ | 153–158 |
| H | H | H | N(CH₃)₂ | —C(O)CH₂CH₃ | 102–109 |
| H | H | H | N(CH₃)₂ | —C(O)CH=C(CH₃)₂ | 127–130 |

-continued

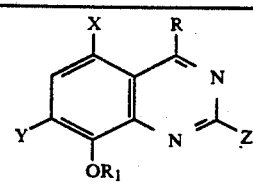

| X | Y | Z | R | R₁ | mp °C. |
|---|---|---|---|---|---|
| H | H | H | N(CH₃)₂ | —C(O)C(=CH₂)CH₃ | 54–63 |
| H | H | H | N(CH₃)₂ | —C(O)CH=CHCH₃ (trans) | 129–133 |
| H | H | H | N(CH₃)₂ | —C(O)C(CH₃)=CH₂ | 117–127 |
| H | H | H | N(CH₃)₂ | —C(O)C₆H₅ | 86–96 |
| H | H | H | N(CH₃)₂ | —C(O)C(Br)=CH₂ | 105–137 |
| H | H | H | N(CH₃)₂ | —C(O)CH(CH₃)₂ | 79–82 |
| H | H | H | N(CH₃)₂ | —C(O)C(CH₃)₃ | 76–78 |
| H | H | CF₃ | N(CH₃)₂ | —C(O)CH=CH₂ | 117.3–117.6 |
| Cl | H | H | OCH(CH₃)₂ | —C(O)CH=CH₂ | 86.9–87.4 |
| Cl | H | H | OCH(CH₃)₂ | —C(O)CH₃ | 78.2–78.5 |
| Cl | H | H | OCH₃ | —C(O)CH=CH₂ | 110.2–110.4 |
| Cl | H | H | O(CH₂)₂CH₃ | —C(O)CH=CH₂ | 70.7–71.4 |
| H | H | CH₃ | N(CH₃)₂ | —C(O)CH=CH₂ | 143.3–144.3 |
| H | H | H | N(CH₃)₂ | —C(O)OCH₃ | 123–128 |
| Cl | H | H | N(CH₃)₂ | —C(O)CH=C(CH₃)₂ | 144–147 |
| CH₃ | H | H | N(CH₃)₂ | —C(O)CH=CH₂ | oil |
| CH₃ | H | H | OCH₃ | —C(O)CH=CH₂ | 93–98 |
| Cl | Br | H | N(CH₃)₂ | —C(O)CH=CH₂ | green solid |
| H | H | H | N(CH₃)₂ | —C(O)-cyclopropyl | 124–128 |

EXAMPLE 6

Preparation of
5-Chloro-4-(dimethylamino)-8-quinazolinol, hydrochloride

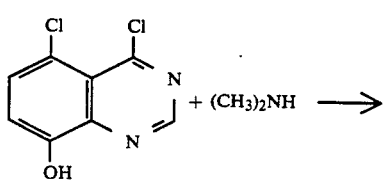

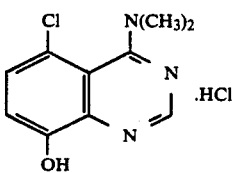

A solution of 4,5-Dichloro-8-quinazolinol (0.6 g, 2.8 mmol) in dichloromethane is added to a saturated solution of dimethylamine gas in dichloromethane. The reaction mixture is stirred for 30 minutes, re-saturated with dimethylamine gas, stirred for 30 minutes and concentrated in vacuo to obtain a yellow solid. The solid is added to a 2.5% hydrochloric acid/ethyl acetate mixture. The mixture is filtered and the filter cake is washed with water and dried in a vacuum oven to give the title product as a white solid, 0.35 g, mp 232° C. (dec.).

Using essentially the same procedure and employing the appropriate amine, the following compounds are obtained:

| R | mp °C. |
|---|---|
| —N⟨pyrrolidine⟩ | 243 (dec.) |
| —N⟨morpholine⟩ | 245 (dec.) |

EXAMPLE 7

Preparation of
5-Chloro-4-(dimethylamino)-8-quinazolinol, sodium salt

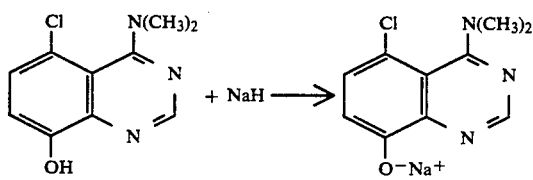

A 60% sodium hydride dispersion in mineral oil (0.043 g, 1.08 mmol) is washed with heptane and suspended in tetrahydrofuran. 5-Chloro-4-(dimethylamino)-8-quinazolinol (0.225 g, 1.01 mmol) is added to the suspension and the reaction mixture is stirred until gas evolution stops. The reaction mixture is then filtered and the filtrate is concentrated in vacuo to obtain the title product as a yellow solid, mp >240° C. (dec).

Using essentially the same procedure and employing the appropriately substituted 5,7-dibromo-8-quinazolinol, the following compounds are obtained:

| R | Color/State |
|---|---|
| —N(CH₃)₂ | yellow solid |
| —N⟨morpholine⟩ | green solid |

EXAMPLE 8

Preparation of
5-chloro-4-(dimethylamino)-8-quinazolinol,
tetrabutylamonium salt

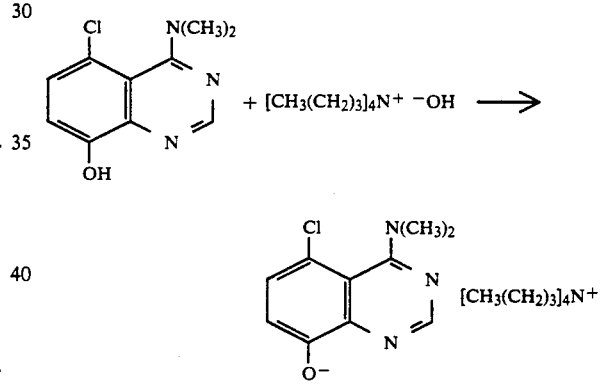

A solution of 5-chloro-4-(dimethylamino)-8-quinazolinol (0.45 g, 2.01 mmol) and a 40% tetrabutylammonium hydroxide solution (1.0 go 1.54 mmol) in dichloromethane is stirred for 10 minutes at room temperature, washed sequentially with water and brine, dried over Na₂SO₄ and concentrated in vacuo to obtain the title product as a green oil, 0.35 g, which is identified by ¹HNMR spectral analysis.

EXAMPLE 9

Preparation of 4-(Dimethylamino)-8-quinazolinyl, methylcarbamate

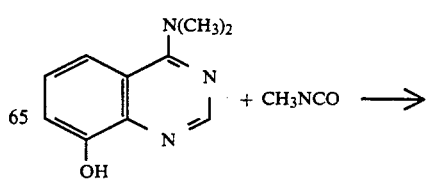

-continued

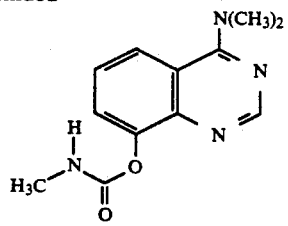

A mixture of 4-(dimethylamino)-8-quinazolinol (0.75 g, 3.96 mmol) in toluene is heated to 40° C. and filtered. The filtrate is cooled to room temperature, treated with methyl isocyanate (0.23 g, 4.03 mmol), stirred for three hours and filtered to obtain the title product as a white solid, 0.4 g, mp 163°-169° C.

Using essentially the same procedure and employing the appropriately substituted isocyanate, the following compounds are obtained:

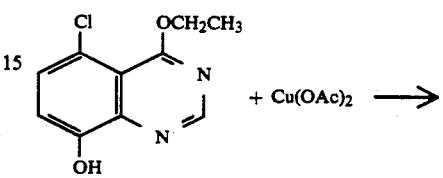

| $R_1$ | mp °C. |
|---|---|
| —C(O)N—phenyl | 132–135 |
| —C(O)N(CH$_2$)$_3$CH$_3$ | 119–124 |
| —C(O)NCH(CH$_3$)$_2$ | 128–135 (dec.) |

EXAMPLE 10

Preparation of 7-Bromo-5-chloro-4-(dimethylamino)-8-quinasolinol, (Fecl$_2$)-1 salt, compound with NaCl (1:1)

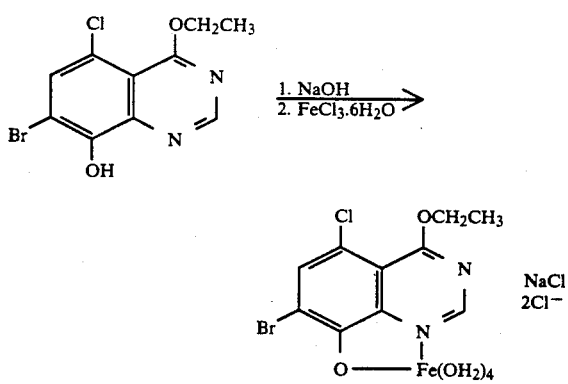

Sodium hydroxide solution (1.0 mL, 1.5 molar) is added to a suspension of 7-bromo-5-chloro-4-(dimethylamino)-8-quinazolinol (0.45 g, 1.49 mmol) in water. The mixture is stirred for 10 minutes and filtered. The filtrate is added to a solution of ferric chloride hexahydrate (0.402 g, 1.49 mmol) in water. The reaction mixture is sonicated for 5 minutes, poured into a dish and allowed to dry for 72 hours to give the title product as a dark green solid, 0.802 g, which is identified by $^1$HNMR spectral analysis.

Using essentially the same procedure and substituting 5-chloro-4-(dimethylamino)-8-quinazolinol as starting material, 5-chloro-4-(dimethylamino)-8-quinazolinol, (FeCl$_2$)-1 salt, compound with NaCl (1:1) is obtained as a dark green solid.

EXAMPLE 11

Preparation of 5-Chloro-4-ethoxy-8-quinazolinol, copper II chelate (2:1)

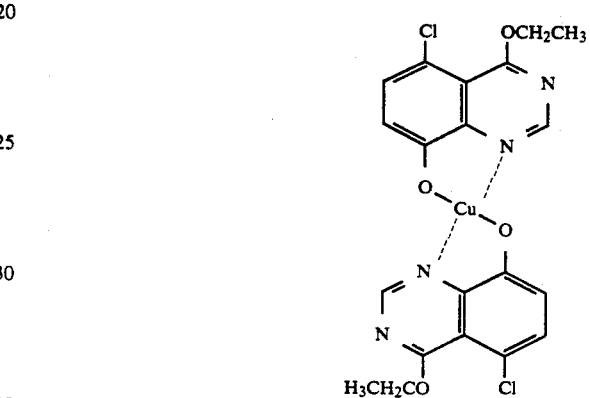

A solution of 5-chloro-4-ethoxy-8-quinazolinol (0.50 g, 2.23 mmol) in chloroform is diluted with ethanol, sonicated for 5 minutes; treated with a solution of copper (II) acetate monohydrate (0.223 g, 1.12 mmol) in water, sonicated at 35° C. for 5 minutes, cooled to room temperature and centrifuged to obtain a solid. The solid is washed with ethanol and dried in a vacuum oven to give the title product as a yellow-green solid, 0.3 g, mp >300° C.

Using essentially the same procedure and substituting 5-chloro-4-isopropoxy-8-quinazolinol as starting material, 5-chloro-4-isopropoxy-8-quinazolinol, copper chelate (2:1) is obtained as a green solid, mp >300° C.

EXAMPLE 12

Evaluation of In Vivo Fungicidal Activity of Test Compounds

Test compounds are dissolved in acetone and diluted with deionized water containing about 0.05% TWEEN 20 ®, a polyoxyethylens sorbitan monolaurate surfactant manufactured by Atlas Chemical Industries, to give a concentration of 400 ppm. Subsequent dilutions are made with an 0.05% aqueous solution of TWEEN 20 ®.

Host plants are sprayed with test solution, dried and inoculated with fungi. When disease symptom development is optimal, the plants are rated for disease control according to the rating scale shown below. Each test contains inoculated treated plants, inoculated untreated plants and a reference standard. When more than one test is run, the data are averaged. The data obtained are shown in Table I.

| RATING SCALE | |
|---|---|
| Rating | Range % Control |
| 0 | 0 |
| 1 | 1–14 |
| 2 | 15–29 |
| 3 | 30–44 |
| 4 | 45–59 |
| 5 | 60–74 |
| 6 | 75–89 |
| 7 | 90–95 |
| 8 | 96–99 |
| 9 | 100 |
| — | no evaluation |

| PHYTOPATHOGENIC FUNGI | | |
|---|---|---|
| Symbol | Disease | Pathogen |
| AS | Apple Scab | *Venturia inaequalis* |
| GDM | Grape Downy Mildew | *Plasmopara viticola* |
| PB | Pepper Botrytis | *Botrytis cinerea* |
| RB | Rice Blast | *Pyricularia oryzae* |
| SBC | Sugar Beet Cercospora | *Cercospora beticola* |
| TLB | Tomato Late Blight | *Phytophthora infestans* |
| TEB | Tomato Early Blight | *Alternaria solani* |
| WLR | Wheat Leaf Rust | *Puccinia recondita* f. sp. *tritici* |
| WPM | Wheat Powdery Mildew | *Erysiphe graminis* f. sp. *tritici* |

TABLE I

In Vivo Fungicidal Evaluations

| Compound | Rate (ppm) | AS | GDM | PB | RB | SBC | TLB | TEB | WLR | WPM |
|---|---|---|---|---|---|---|---|---|---|---|
| 5-Chloro-4-(dimethylamino)-8-quinazolinol, hydrochloride | 400 | 9.0 | 8.0 | 8.5 | 4.0 | 1.5 | 7.0 | — | 8.0 | 8.5 |
| 5-Chloro-4-(1-pyrrolidinyl)-8-quinazolinol, hydrochloride | 400 | 9.0 | 7.5 | 4.7 | 7.5 | 6.0 | 5.5 | — | 8.3 | 7.7 |
| 5-Chloro-4-morpholino-8-quinazolinol, hydrochloride | 400 | 6.5 | 8.0 | 6.5 | 8.5 | 7.0 | 0.0 | — | 8.0 | 8.0 |
| 5-Chloro-4-(dimethylamino)-8-quinazolinol | 400 | 8.0 | 7.0 | 6.7 | 7.5 | 4.0 | 5.5 | — | 8.0 | 9.0 |
| 7-Bromo-5-chloro-4-(dimethylamino)-8-quinazolinol | 400 | 6.0 | 7.3 | 7.0 | 8.0 | 2.7 | 2.3 | — | 7.6 | 7.8 |
| 4-(Dimethylamino)-8-quinazolinol | 400 | 9.0 | 7.5 | 7.0 | 3.0 | 8.0 | 2.0 | — | 4.5 | 2.0 |
| 4-Morpholino-8-quinazolinol | 400 | 8.0 | 6.0 | 7.5 | 7.5 | 8.0 | 3.5 | — | 5.5 | 4.0 |
| 4-(1-Pyrrolidinyl)-8-quinazolinol | 400 | 9.0 | 4.0 | 7.0 | 4.0 | 8.0 | 3.5 | — | 4.0 | 1.0 |
| 4-Piperidino-8-quinazolinol | 400 | 8.0 | 8.0 | 8.0 | 7.0 | 6.0 | 7.0 | — | 7.0 | 0.0 |
| 5-Chloro-4-(dimethylamino)-8-quinazolinol, sodium salt | 400 | 9.0 | 6.0 | 8.0 | 4.0 | 4.0 | 6.0 | — | 7.0 | 9.0 |
| 7-Bromo-5-chloro-4-(dimethylamino)-8-quinazolinol, $(FeCl_2)$-1 salt, compound with NaCl (1:1) | 400 | 0.0 | 0.0 | 0.0 | 0.0 | 0.0 | 0.0 | — | 0.0 | 0.0 |
| 5-Chloro-4-(dimethylamino)-8-quinazolinol, $(FeCl_2)$-1 salt, compound with NaCl (1:1) | 400 | 0.0 | 6.0 | 7.5 | 0.0 | 8.0 | 0.0 | — | 0.0 | 0.0 |
| 5,7-Dibromo-4-(dimethylamino)-8-quinazolinol | 400 | 4.0 | 4.0 | 7.5 | 4.5 | 3.0 | 5.0 | — | 7.0 | 9.0 |
| 5,7-Dibromo-4-(dimethylamino)-8-quinazolinol, sodium salt | 400 | 7.0 | 6.0 | 4.0 | 4.0 | 0.0 | 0.0 | — | 7.0 | 7.0 |
| 5,7-Dibromo-4-morpholino-8-quinazolinol | 400 | 4.0 | 2.0 | 3.5 | 2.0 | 5.0 | 0.0 | — | 6.0 | 3.0 |
| 5,7-Dibromo-4-morpholino-8-quinazolinol, sodium salt | 400 | 6.0 | 0.0 | 0.0 | 4.0 | 0.0 | 0.0 | — | 4.0 | 0.0 |
| 5,7-Dibromo-4-(1-pyrrolidinyl)-8-quinazolinol, hydrochloride | 400 | 4.0 | 4.0 | 7.0 | 4.0 | 0.0 | 0.0 | — | 7.0 | 0.0 |
| 5-Chloro-4-isopropoxy-8-quinazolinol | 400 | 0.0 | 0.0 | 3.0 | 5.0 | 5.0 | 7.0 | — | 6.0 | 4.5 |
| 5-Chloro-4-ethoxy-8-quinazolinol, copper II chelate | 400 | 0.0 | 0.0 | 0.0 | 0.0 | 0.0 | — | — | 0.0 | 0.0 |
| 5-Chloro-4-propoxy-8-quinazolinol | 400 | 2.0 | 0.0 | 0.0 | 4.3 | 1.7 | 4.0 | — | 5.0 | 6.3 |
| 5-Chloro-4-ethoxy-8-quinazolinol | 400 | 0.0 | 3.5 | 3.0 | 3.0 | 5.5 | 0.0 | — | 6.0 | 7.0 |
| 5-Chloro-4-isopropyl-8-quinazolinyl acrylate | 400 | 0.0 | 4.5 | 0.0 | 6.5 | 3.5 | 0.0 | — | 7.5 | 8.5 |
| 5-Chloro-4-isopropoxy-8-quinazolinol acetate | 400 | 7.0 | 0.0 | 7.0 | 0.0 | 0.0 | — | — | 0.0 | 9.0 |
| 5-Chloro-4-methoxy-8-quinazolyl acrylate | 400 | 4.0 | 7.5 | 5.0 | 7.5 | 6.0 | 6.0 | — | 8.5 | 9.0 |
| 5-Chloro-4-propoxy-8-quinazolyl acrylate | 400 | 0.0 | 4.0 | 1.0 | 2.0 | 0.0 | 0.0 | — | 8.0 | 7.5 |
| 5-Chloro-4-methoxy-8-quinazolinol | 400 | 0.0 | 1.0 | 5.0 | 5.5 | 2.0 | 6.0 | — | 5.5 | 8.0 |
| 5-Chloro-4-isopropoxy-8-quinazolinol, copper chelate (2:1) | 400 | 4.0 | 9.0 | 0.0 | 0.0 | 0.0 | 0.0 | — | 0.0 | 0.0 |
| 4-(Dimethylamino)-5-methyl-8-quinazolinyl acrylate | 400 | — | 8.0 | 4.0 | 5.0 | 8.0 | 4.0 | — | 7.0 | 0.0 |
| 5-Chloro-4-methyl-8-quinazolinol | 400 | — | 0.0 | 4.0 | 4.0 | 0.0 | 4.0 | — | 0.0 | 0.0 |
| 4-Methyloxy-5-methyl-8-quinazolinyl acrylate | 400 | — | 0.0 | 4.0 | 4.0 | 0.0 | 0.0 | — | 8.0 | 4.0 |

TABLE I-continued

| Compound | Rate (ppm) | AS | GDM | PB | RB | SBC | TLB | TEB | WLR | WPM |
|---|---|---|---|---|---|---|---|---|---|---|
| 4-Methoxy-5-methyl-8-quinazolinol | 400 | — | 0.0 | 7.0 | 0.0 | 0.0 | 4.0 | — | 4.0 | 0.0 |
| 4-(Dimethylamino)-5-methyl-8-quinazolinol | 400 | — | 9.0 | 6.0 | 4.0 | 7.0 | 0.0 | — | 4.0 | 2.0 |
| 5-Chloro-4-(dimethylamino)-8-quinazolinyl acrylate | 400 | 9.0 | 4.5 | 2.5 | 8.0 | 5.0 | 0.0 | — | 4.5 | 9.0 |
| 5-Chloro-4-(dimethylamino)-8-quinazolinyl 3-methylcrotonate | 400 | 0.0 | 3.0 | 5.0 | 0.0 | 8.0 | 0.0 | — | 0.0 | 0.0 |
| 5-Chloro-4-(dimethylamino)-8-quinazolinol, tetrabutylammonium salt | 400 | 8.0 | 4.0 | 0.0 | 0.0 | 6.0 | — | — | 4.0 | 0.0 |
| 4-(Dimethylamino)-8-quinazolinyl acrylate | 400 | 8.5 | 7.5 | 0.0 | 7.0 | 8.0 | 0.0 | — | 0.0 | 3.0 |
| 7-Bromo-5-chloro-4-(dimethylamino)-8-quinazolinyl acrylate | 400 | 8.0 | 5.0 | 7.0 | 6.5 | 0.0 | 0.0 | — | 7.5 | 8.0 |
| 4-(Dimethylamino)-8-quinazolinyl propionate | 200 | 8.5 | 6.0 | 3.0 | 0.0 | 0.0 | — | 7.5 | 7.0 | 3.0 |
| 4-(Dimethylamino)-8-quinazolinyl 3-methylcrotonate | 200 | 6.5 | 0.0 | 3.0 | 0.0 | 3.0 | — | 6.5 | 5.0 | 0.0 |
| 4-(Dimethylamino)-8-quinazolinyl 2-methylacrylate | 200 | 0.0 | 5.0 | 0.0 | 0.0 | 0.0 | — | 6.0 | 7.0 | 0.0 |
| 4-(Dimethylamino)-8-quinazolinyl cyclopropanecarboxylate | 200 | 8.0 | 6.0 | 6.0 | 0.0 | 0.0 | — | 8.0 | 7.0 | 0.0 |
| 4-(Dimethylamino)-8-quinazolinyl crotonate, (E)- | 200 | 6.0 | 5.0 | 5.0 | 0.0 | — | — | 7.0 | 7.0 | 6.0 |
| 4-(Dimethylamino)-8-quinazolinyl methylcarbamate | 200 | 0.0 | 7.0 | 5.0 | 0.0 | — | — | 6.0 | 6.0 | 6.0 |
| 4-(Dimethylamino)-8-quinazolinol benzoate | 200 | 8.0 | 6.0 | 8.0 | 0.0 | — | — | 7.0 | 6.0 | 6.0 |
| 4-(Dimethylamino)-2-(trifluoromethyl)-8-quinazolinol | 200 | 0.0 | 0.0 | 0.0 | 0.0 | 0.0 | — | 0.0 | 0.0 | 0.0 |
| 4-(Dimethylamino)-2-(trifluoromethyl)-8-quinazolinyl acrylate | 200 | 7.0 | 6.0 | 0.0 | 0.0 | 0.0 | — | 0.0 | 7.0 | 5.0 |
| 4-(Dimethylamino)-2-methyl-8-quinazolinyl acrylate | 200 | 8.0 | 5.0 | 0.0 | 0.0 | 0.0 | — | 7.0 | 0.0 | 0.0 |
| 4-(Dimethylamino)-2-methyl-'8-quinazolinol | 200 | 0.0 | 0.0 | 0.0 | 0.0 | 0.0 | — | 6.0 | 0.0 | 0.0 |
| 4-(Dimethylamino)-8-quinazolinyl methylcarbonate | 200 | 8.0 | 3.0 | 0.0 | 0.0 | 8.0 | — | 7.0 | 2.0 | 0.0 |
| 4-(Dimethylamino)-8-quinazolinyl 2-bromoacrylate | 200 | 9.0 | 7.0 | 7.0 | 0.0 | 9.0 | — | 0.0 | 2.0 | 0.0 |
| 4-(Dimethylamino)-8-quinazolinyl phenylcarbamate | 200 | 9.0 | 9.0 | 7.0 | 6.0 | 6.0 | — | 6.0 | 2.0 | 0.0 |
| 4-(Dimethylamino)-8-quinazolinyl butylcarbamate | 200 | 9.0 | 7.0 | 7.0 | 7.0 | 7.0 | — | 6.0 | 6.0 | 0.0 |
| 4-(Dimethylamino)-8-quinazolinyl isobutyrate | 200 | 9.0 | 7.0 | 9.0 | 8.0 | 3.0 | — | 9.0 | 6.0 | 0.0 |
| 4-(Dimethylamino)-8-quinazolinyl pivalate | 200 | 8.0 | 9.0 | 9.0 | 0.0 | 5.0 | — | 9.0 | 6.0 | 0.0 |
| 4-(Dimethylamino)-8-quinazolinyl isopropylcarbamate | 200 | 8.0 | 8.0 | 8.0 | 7.0 | — | — | 8.0 | 8.0 | 3.0 |

EXAMPLE 13

Evaluation of In Vitro Fungicidal Activity of Test Compounds

Test compounds are dissolved in acetone and dispersed into cell well plates containing a suspension of ground fungal mycelium in a nutrient broth. Assay plates are incubated for 3-4 days at 21° C. Growth inhibition is measured visually and is rated using the following scale:

| Rating | % Inhibition |
|---|---|
| 0 | 0 |
| 1 | 1–29 |
| 3 | 30–59 |
| 5 | 60–89 |
| 7 | 90–99 |
| 9 | 100 |

Untreated controls, solvent blanks and reference standards are included in each test.

Assay fungi include the plant pathogens, *pythium ultimum* (Pythul) and *Rhizoctonia solani* (Rhizso).

TABLE II

| | In Vitro Fungicidal Evaluations | |
|---|---|---|
| Compound | PYTHUL (25 ppm) | RHIZSO (25 ppm) |
| 5-Chloro-4-(dimethylamino)-8-quinazolinol, hydrochloride | 8.0 | 9.0 |
| 5-Chloro-4-(1-pyrrolidinyl)-8-quinazolinol, hydrochloride | 8.0 | 9.0 |
| 5-Chloro-4-morpholino-8-quina- | 8.0 | 4.5 |

TABLE II-continued

In Vitro Fungicidal Evaluations

| Compound | PYTHUL (25 ppm) | RHIZSO (25 ppm) |
|---|---|---|
| zolinol, hydrochloride | | |
| 5-Chloro-4-(dimethylamino)-8-quinazolinol | 9.0 | 9.0 |
| 7-Bromo-5-chloro-4-(dimethylamino)-8-quinazolinol | 9.0 | 8.3 |
| 4-(Dimethylamino)-8-quinazolinol | 4.5 | 9.0 |
| 4-Morpholino-8-quinazolinol | 8.0 | 9.0 |
| 4-(1-Pyrrolidinyl)-8-quinazolinol | 4.5 | 9.0 |
| 5-Chloro-4-(dimethylamino)-8-quinazolinol, (FeCl$_2$)-1 salt, compound with NaCl (1:1) | 5.0 | 9.0 |
| 5,7-Dibromo-4-(dimethylamino)-8-quinazolinol | 4.5 | 1.5 |
| 5,7-Dibromo-4-(dimethylamino)-8-quinazolinol, sodium salt | 9.0 | 0.0 |
| 5,7-Dibromo-4-morpholino-8-quinazolinol | 4.5 | 1.5 |
| 5,7-Dibromo-4-morpholino-8-quinazolinol, sodium salt | 9.0 | 0.0 |
| 5,7-Dibromo-4-(1-pyrrolidinyl)-8-quinazolinol, hydrochloride | 9.0 | 3.0 |
| 5-Chloro-4-propoxy-8-quinazolinol | 0.0 | 1.5 |
| 5-Chloro-4-isopropyl-8-quinazolinyl acrylate | 3.0 | 4.0 |
| 5-Chloro-4-methoxy-8-quinazolyl acrylate | 3.0 | 8.0 |
| 5-Chloro-4-propoxy-8-quinazolyl acrylate | 3.0 | 3.3 |
| 5-Chloro-4-methoxy-8-quinazolinol | 0.0 | 5.0 |
| 4-(Dimethylamino)-5-methyl-8-quinazolinyl acrylate | 3.5 | 4.5 |
| 5-Chloro-4-methyl-8-quinazolinol | 3.5 | 4.5 |
| 4-Methyloxy-5-methyl-8-quinazolinyl acrylate | 0.0 | 3.0 |
| 4-Methoxy-5-methyl-8-quinazolinol | 4.5 | 4.5 |
| 4-(Dimethylamino)-5-methyl-8-quinazolinol | 4.5 | 8.0 |
| 5-Chloro-4-(dimethylamino)-8-quinazolinyl acrylate | 4.5 | 4.5 |
| 5-Chloro-4-(dimethylamino)-8-quinazolinyl 3-methylcrotonate | 8.0 | 9.0 |
| 5-Chloro-4-(dimethylamino)-8-quinazolinol, tetrabutylammonium salt | 9.0 | 9.0 |
| 4-(Dimethylamino)-8-quinazolinyl acrylate | 9.0 | 9.0 |
| 7-Bromo-5-chloro-4-(dimethylamino)-8-quinazolinyl acrylate | 9.0 | 9.0 |
| 4-(Dimethylamino)-8-quinazolinol propionate | 1.0 | 4.3 |
| 4-(Dimethylamino)-8-quinazolinyl cyclopropanecarboxylate | 0.0 | 3.0 |
| 4-(Dimethylamino)-8-quinazolinyl crotonate, (E)- | 0.0 | 3.0 |
| 4-(Dimethylamino)-8-quinazolinyl methylcarbamate | 6.0 | 2.5 |
| 4-(Dimethylamino)-8-quinazolinol benzoate | 5.0 | 3.0 |
| 4-(Dimethylamino)-2-(trifluoromethyl)-8-quinazolinyl acrylate | 3.0 | 0.0 |
| 4-(Dimethylamino)-8-quinazolinyl methylcarbonate | 0.0 | 3.0 |
| 4-(Dimethylamino)-8-quinazolinyl 2-bromoacrylate | 0.0 | 3.0 |
| 4-(Dimethylamino)-8-quinazolinyl isopropylcarbamate | 9.0 | 3.0 |

I claim:

1. A compound having the structure

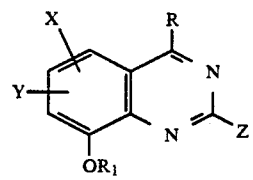

wherein

X, Y and Z are each independently hydrogen, halogen,
$C_1$–$C_6$ alkyl optionally substituted with one or more halogen atoms,
$C_1$–$C_6$ alkoxy optionally substituted with one or more halogen atoms,
nitro, or
cyano;

R is $NR_2R_3$ or $AR_4$;

A is O or S;

$R_2$ and $R_3$ are each independently hydrogen,
$C_1$–$C_6$ alkyl optionally substituted with one or more halogen atoms, nitro groups, cyano groups, or
$C_1$–$C_4$ alkoxy groups optionally substituted with one or more halogen atoms, or
phenyl optionally substituted with one to three halogen atoms, nitro groups, cyano groups, $C_1$–$C_4$ alkyl groups optionally substituted with one or more halogen atoms, or $C_1$–$C_4$ alkoxy groups optionally substituted with one or more halogen atoms; and, when taken together, $R_2$ and $R_3$ may form a 5- or 6-membered ring in which $R_2R_3$ is represented by the structure: —$(CH_2)_n$—, optionally interrupted by one heteroatom selected from O, S and N, where n is an integer of 3, 4 or 5;

$R_4$ is $C_1$–$C_6$ alkyl optionally substituted with one to three halogen atoms, nitro groups, cyano groups, or $C_1$–$C_4$ alkoxy groups optionally substituted with one or more halogen atoms, or
phenyl optionally substituted with one to three halogen atoms, nitro groups, cyano groups, $C_1$–$C_4$ alkyl groups optionally substituted with one or more halogen atoms, or $C_1$–$C_4$ alkoxy groups optionally substituted with one or more halogen atoms;

$R_1$ is hydrogen, $$-\overset{\overset{\displaystyle O}{\|}}{C}R_5$$

or is a metal, ammonium or organic ammonium cation in which 1–4 aliphatic hydrocarbon groups monovalently are attached to the nitrogen;

$R_5$ is $C_1$–$C_6$ alkyl optionally substituted with one to three halogen atoms, or $C_1$–$C_4$ alkoxy groups optionally substituted with one or more halogen atoms,
$C_2$–$C_6$ alkenyl optionally substituted with one to three halogen atoms,
$C_3$–$C_6$ cycloalkyl optionally substituted with one to three halogen atoms, $C_1$–$C_4$ alkyl groups optionally substituted with one or more halogen atoms, or $C_1$–$C_4$ alkoxy groups optionally substituted with one or more halogen atoms, phenyl optionally substituted with one to three halogen atoms, nitro groups, cyano groups, $C_1$-$C_4$ alkyl groups optionally substituted with one or more halogen atoms, or $C_1$-$C_4$ alkoxy groups optionally substituted with one or more halogen atoms, $NHR_6$, or $OR_6$;

$R_6$ is $C_1$-$C_6$ alkyl optionally substituted with one to three halogen atoms, or $C_1$-$C_4$ alkoxy groups optionally substituted with one or more halogen atoms, or phenyl optionally substituted with one to three halogen atoms, nitro groups, cyano groups, $C_1$-$C_4$ alkyl groups optionally substituted with one or more halogen atoms, or $C_1$-$C_4$ alkoxy groups optionally substituted with one or more halogen atoms;

the acid addition salts thereof when $R_1$ is other than a cation;

the metal salts thereof; and the metal chelates thereof;

with the proviso that when $R_2$ or $R_3$ is hydrogen, then X, Y, Z and $R_1$ cannot be hydrogen; and when X, Y, Z and $R_1$ are hydrogen, then $R_2R_3$ cannot represent the structure: —$(CH_2)_5$—.

2. The compound according to claim 1 wherein the compound has the structure

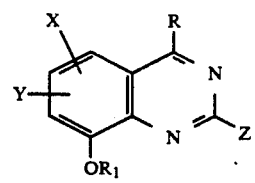

3. The compound according to claim 2 wherein
X is hydrogen, halogen or $C_1$-$C_6$ alkyl;
Y is hydrogen or halogen;
Z is hydrogen or $C_1$-$C_6$ alkyl optionally substituted with one or more halogen atoms;
R is $NR_2R_3$ or $AR_4$;
A is O;
$R_2$ and $R_3$ are each independently $C_1$-$C_6$ alkyl; and, when taken together, $R_2$ and $R_3$ may form a 5- or 6-membered ring in which $R_2R_3$ is represented by the structure: —$(CH_2)_n$—, optionally interrupted by O, where n is an integer of 3, 4 or 5;
$R_4$ is $C_1$-$C_6$ alkyl;
$R_1$ is hydrogen,

or an alkali metal, ammonium or organic ammonium cation;
$R_5$ is $C_1$-$C_6$ alkyl, $C_3$-$C_6$ cycloalkyl, phenyl, $NHR_6$, $OR_6$ or $C_2$-$C_6$ alkenyl optionally substituted with one halogen atom; and
$R_6$ is $C_1$-$C_6$ alkyl or phenyl.

4. The compound according to claim 3 selected from the group consisting of 4-(dimethylamino)-8-quinazolinol, 4-(dimethylamino)-8-quinazolinyl acrylate, 5-chloro-4-(dimethylamino)-8-quinazolinol, 4-(dimethylamino)-8-quinazolinyl isobutyrate and 4-(dimethylamino)-8-quinazolinyl pivalate.

* * * * *